United States Patent [19]

Reichenberger

[11] 3,998,212

[45] Dec. 21, 1976

[54] ELECTRODE FOR PERCUTANEOUS POLAROGRAPHIC MEASUREMENTS

[75] Inventor: Helmut Reichenberger, Brand, Germany

[73] Assignee: Siemens Aktiengesellschaft, Erlangen, Germany

[22] Filed: May 30, 1975

[21] Appl. No.: 582,422

[30] Foreign Application Priority Data

June 28, 1974 Germany ............ 7422154[U]

[52] U.S. Cl. .................. 128/2 E; 128/2.1 E; 204/195 B; 204/195 P
[51] Int. Cl.² ............................... A61B 5/00
[58] Field of Search ............ 128/2 E, 2 L, 2.1 E, 128/2.06 E, 417, 418, DIG. 4, 2 H, 303.1, 362, 379, 399; 204/195 B, 195 P

[56] References Cited

UNITED STATES PATENTS

| | | | |
|---|---|---|---|
| 1,752,117 | 3/1930 | Smith | 128/2 H |
| 2,798,493 | 7/1957 | Sukacev | 128/379 |
| 2,938,356 | 5/1960 | McMahon | 128/399 |
| 3,605,722 | 9/1971 | Riseman et al. | 128/2.1 E |
| 3,659,586 | 5/1972 | Johns et al. | 128/2.1 E |
| 3,795,239 | 3/1974 | Eberhard et al. | 128/2 E |
| 3,882,853 | 5/1975 | Gofman et al. | 128/2.1 E |
| 3,918,434 | 11/1975 | Lubbers et al. | 128/2 E |

*Primary Examiner*—Robert W. Michell
*Assistant Examiner*—Lee S. Cohen
*Attorney, Agent, or Firm*—Haseltine, Lake & Waters

[57] ABSTRACT

An electrode for percutaneous polarographic measurements and, in particular, an oxygen electrode for the percutaneous measurement of the partial pressure or tension of oxygen in human or animal bodies, including a carrier or support portion for the actual measuring electrode as well as, if the case requires, for the reference electrode; a gas-permeable membrane forming an electrode covering on the application side of the latter; an electrolyte introduced between the membrane and the electrode application surface, as well as connectors for the connection of the measuring electrode, respectively, the reference electrode, to a power supply and measuring unit. Only the measuring electrode is covered with a membrane merely on the application side thereof for the enclosure of an electrolyte, and the thus membrane-covered measuring electrode is inserted into a recess which is formed in the carrier portion so as to be readily separated from the carrier portion.

9 Claims, 1 Drawing Figure

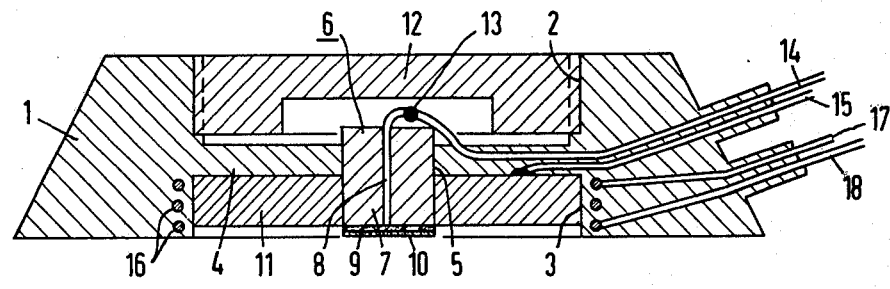

ELECTRODE FOR PERCUTANEOUS POLAROGRAPHIC MEASUREMENTS

FIELD OF THE INVENTION

The present invention relates to an electrode for percutaneous polarographic measurements and, in particular, an oxygen electrode for the percutaneous measurement of the partial pressure or tension of oxygen in human or animal bodies, including a carrier or support portion for the actual measuring electrode as well as, if the case requires, for the reference electrode; a gas-permeable membrane forming an electrode covering on the application side of the latter; an electrolyte introduced between the membrane and the electrode application surface, as well as connectors for the connection of the measuring electrode, respectively, the reference electrode, to a power supply and measuring unit.

DISCUSSION OF THE PRIOR ART

There are presently known $pO_2$ measuring electrodes of this type, in which the entire application surface of the electrode, meaning, the carrier portion and also the actual measuring electrode (cathode), as well as the counterelectrode (anode), is completely covered with a membrane for the enclosure of an electrolyte. This constructive electrode arrangement is, however, extremely disadvantageous, for example, with respect to measuring electrode (cathodes) defects which may possibly occur, in particular due to contaminations, since, in each instance, for eliminating these defects, there must first be removed the membrane and electrolyte from the electrode carrier portion and, after elimination of the defects, must be again completely and complexly reassembled. Subsequently, the entire electrode must then be renewedly calibrated.

SUMMARY OF THE INVENTION

Accordingly, it is an object of the present invention to obviate the advantages encountered in the prior art, meaning in effect, to construct an electrode which facilitates a less complex elimination of electrode defects.

The foregoing object is inventively attained in that only the measuring electrode is covered with a membrane merely on the application side thereof for the enclosure of an electrolyte, and the thus membrane-covered measuring electrode is inserted into a recess which is formed in the carrier portion so as to be readily separated from the carrier portion.

The electrode constructed in accordance with the present invention, through a simple exchange of the membrane-covered measuring electrode (total replacement, facilitates the elimination of defects; complex prior disassembly and reassembly of the membrane and electrolyte are thereby obviated. The electrode constructed pursuant to the invention thereby becomes essentially easier to handle and is commercially less expensive than known electrodes. Coming into consideration as the interchangeable components are electrodes which have already been previously calibrated, meaning, preferably by the manufacturer. There may thus be omitted the complex after-calibrations of the electrode prior to placing the latter into operation.

BRIEF DESCRIPTION OF THE DRAWING

Further advantages and details of the invention may now be ascertained from the following description of an exemplary embodiment thereof, taken in conjunction with the accompanying single FIGURE of the drawing which illustrates a sectional view of an electrode constructed pursuant to the invention.

DETAILED DESCRIPTION

Referring in detail to the drawing, reference numeral 1 designates a plastic material carrier portion for the electrode, which is provided with annular recesses 2 and 3 formed in, respectively, the head and application surfaces thereof. Both recesses 2 and 3 further are connected with each other by means of a bore 5 having a smaller diameter which extends through the remaining intermediate part 4 of the carrier portion 1.

Inserted into this bore 5 in a gas-tight fit from the upper end thereof, meaning extending from the recess 2, is a circularly-shaped measuring electrode 6 (cathode), the latter of which consists of an insulated annular carrier 77 having introduced therein a noble metal wire 8 which, for example, is constituted of gold. The measuring electrode 6, for example, is coated on the application surface thereof with an electrolyte 9, and the latter is covered wth a superimposed gas-permeable electrically conductive membrane 10 constituted, for example, of cellulose acetate.

Furthrore, a ring is located in the recess 3 on the application-sided surface of the electrode, preferably an Ag/AgCl-ring, so as to form the counterelectrode (anode for the measuring electrode 6. The recess 2 in the head-sided surface of carrier portion 1 is, in connection therewith closed off by means of a screw cover 12 (or upon occasion, also by means of a lid or gas-tight sealing putty).

Should the measuring electrode 6 require to be exchanged, for example, due to a defect, then the screw cover 12 merely needs to be screwed out of the recess 2, and the defective measuring electrode 6 pulled out of the bore 5. After the insertion of a new measuring electrode 6 which, for example, has been previously calibrated by the manufacturer, the recess 2 is again closed off by screwing in of the cover 12 (total replacement of the membrane-covered measuring electrode).

For effecting the removal of the measuring electrode 6, the noble metal wire 8 must herein be separated (soldered off) from the conductor wire 14 at the soldering location 13. In lieu of a solder location there may, of course, be employed other types of connections, for example, a clamping connection or the like. The conductor wire 14, together with a further conductor wire 15 which is connected or, for example, soldered to the counterelectrode 11, serves as the connector conductor for effecting the connection of the electrode to a power supply and measuring unit (not shown).

A temperature of the electrode which is elevated in contrast with the normal skin temperature, stabilizes the measurement and provides for the necessary hyperesthesia or hypersensibility of the skin. For the heating of the electrode and the skin, a heating coil 16 is, accordingly, introduced in the electrode carrier portion 1, together with connector conductors 17 and 18. A branch of the conductors 17, 18 is herein constituted of a material which, in conjunction with the heating coil 16, forms a thermocouple for the temperature measurement (for example, winding 16 and conductor 17 being of constantan, and conductor 18 of copper). The second soldering location lies in the operating apparatus, or in a power supply receptacle. Thereby, the number of conductors may be reduced.

While there has been shown what is considered to be the preferred embodiment of the invention, it will be obvious that modifications may be made which come within the scope of the disclosure of the specification.

What is claimed is:

1. In a sensor for percutaneous polarographic measurements having anode and cathode electrodes, including a carrier portion for the electrodes; said carrier portion having a surface adapted to be applied to the skin of a patient and having a recess formed on said surface receiving said electrodes; a gas-permeable membrane mounted on said surface of said carrier portion an electrolyte located between said membrane and said cathode; and connector means for connecting said electrodes to a source of power supply and to a measuring unit, the improvement comprising: said membrane covering the application-facing end surface of only said cathode, said cathode being detachably mounted in said recess formed in said carrier portion, said cathode being isolated only by said membrane and electrolyte from the environment thereof, said anode having direct contact with the environment.

2. A sensor as claimed in claim 1, said membrane comprising an oxygen permeable material for the percutaneous measurement of oxygen tension in human and animal bodies.

3. A sensor as claimed in claim 1, wherein said carrier portion has a head part; and access means formed in the head part of said carrier portion communicating with said recess for inserting said cathode into said recess.

4. A sensor as claimed in claim 3, said access means comprising a recess formed in the head part of said carrier portion and a bore communicating said first and second recesses and extending through the central portion of said carrier portion, said cathode being positioned in said bore.

5. A sensor as claimed in claim 3 comprising screw cover means connected to said access means for sealingly closing said access means.

6. A sensor as claimed in claim 1, comprising soldering locations being provided on said connector means for detaching and attaching said electrodes to said power supply and to said measuring unit.

7. A sensor as claimed in claim 1, comprising a heating coil being located in said carrier portion and in proximity to said electrodes for heating the electrodes and the skin of a patient, and means for connecting said heating coil to a source of current.

8. A sensor as claimed in claim 7, said heating coil comprising coil connections constituted of materials forming a thermocouple for alternatingly heating and temperature measurement and for thermal stabilization.

9. A sensor as claimed in claim 8, said thermocouple materials being essentially constantan and copper.

* * * * *